United States Patent [19]

Stephen et al.

[11] Patent Number: 5,607,940

[45] Date of Patent: Mar. 4, 1997

[54] MORPHINE FORMULATIONS FOR USE BY ELECTROMOTIVE ADMINISTRATION

[76] Inventors: Robert L. Stephen, 2501 Kensington Ave., Salt Lake City, Utah 84108; Cesare Bonezzi, Via Porta Salara, 10-27100 Padova, Italy; Cino Rossi, Via Settala, 32-00123 Roma, Italy; Silvio Eruzzi, Via A. Mori, 23-46100 Mantova, Italy

[21] Appl. No.: 276,613

[22] Filed: Jul. 18, 1994

[51] Int. Cl.$^6$ ................... A61K 31/44; C07D 471/00; C07D 489/00; A61N 1/30
[52] U.S. Cl. ................ 514/282; 546/44; 546/45; 604/20
[58] Field of Search ............... 514/282; 546/44, 546/45; 604/20

[56] References Cited

U.S. PATENT DOCUMENTS

| | | | |
|---|---|---|---|
| 4,248,855 | 2/1981 | Blank | 424/78 |
| 4,626,539 | 12/1986 | Aungst et al. | 514/282 |
| 4,747,819 | 5/1988 | Phipps et al. | 604/20 |
| 4,879,297 | 11/1989 | Mahjour et al. | 514/282 |
| 4,915,685 | 4/1990 | Petelenz et al. | 604/20 |
| 4,968,297 | 11/1990 | Jacobsen et al. | 604/20 |
| 4,979,938 | 12/1990 | Stephen et al. | 604/20 |
| 5,057,072 | 10/1991 | Phipps | 604/20 |
| 5,387,420 | 2/1995 | Mitchell | 424/466 |

FOREIGN PATENT DOCUMENTS 0171742  2/1986  European Pat. Off. .

OTHER PUBLICATIONS

J. Pain Symptom Manage. vol. 7, No. 1, 1992, pp. 27–33. M. A. Ashburn et al, "Iontophoretic Delivery of Morphine for Postoperative Analgesia".
J. Pain Symptom Manag. vol. 7, No. 3, 1992, pp. 160–162. W. S. Nimmo "Novel Delivery Systems: Electrotransport".
Pharm. Res. vol. 5, No. 7, 1988, pp. 443–446 P. Glikfeld et al., "A New System for In Vitro Studies of Iontophoresis".

*Primary Examiner*—John Kight
*Assistant Examiner*—Everett White

[57] ABSTRACT

A morphine formulation for use by electromotive administration comprising morphine citrate salts of the formula:

$$M_{np}Ct_{(3-n)p}(C_6H_5O_7)_p$$

wherein M is protonated morphine, Ct is a physiologically acceptable cation, n is an integer or fractional number greater than 0 and less than or equal to 3, and p is an integer from 1 to 3.

6 Claims, 3 Drawing Sheets

MORPHINE FORMULATIONS FOR USE BY ELECTROMOTIVE ADMINISTRATION

BACKGROUND OF THE INVENTION

The present invention relates to new salts of morphine, for use as analgesic medicament for relief of pain through electromotive administration.

Morphine is the first opioid drug to have been isolated in pure forme and is used clinically as drug to achieve relief of nocioceptive pain, too severe to be controlled by peripheral analgesics such as the salicylates. Morphine with a pKa of 8.2 units, is strongly ionised at a normal blood pH of 7.4 units and has a low lipid solubility. Therefore this drug is slow to enter the CNS, a fact that is readily verified by having to wait at least 10 minutes after an iv bolus injection to observe maximum respiratory depression.

With detailed pharmachological understanding of agonism-antagonism actions at CNS receptor sites as yet very limited, morphine remains the "gold standard" for assessing the efficacy of all other opioid drugs. It is familiar to physicians the world over, very inexpensive and, given in correct dosages for different painful conditions, always exerts a beneficial therapeutic effect with small chance of inducing psychological dependence.

Morphine base is soluble 1/5000 in water and 1/250 ethanol, thus necessitating ionised formulations for aqueous injections of reasonably small volumes. Two ionised forms, morphine sulphate and morphine hydrochloride, are available for clinical use in most countries. Both formulations are soluble in water, 1/20–25, and their main physical difference is in their solubilities in ethanol, 1/1000 and 1/50, respectively. Many other derivatives of morphine have been synthesised and these include: morphine-hydrobromide; methyl bromide; oxide; nitrate; monobasic phosphate; acetate; lactate; meconate; tartrate; valerate; 6-methylether; oleate; hyperduric; ester-nicotinate and hydrochloride-nicotinate. They proved however to be of little clinical utility.

Of the oral formulations of morphine available, slow-release morphine sulphate has proven particularly valuable in the long term management of cancer pain, although the dose must be adjusted to allow for the 60–70% to be metabolised in the intestinal wall and liver before it ever reaches the systemic circulation and hence the CNS.

Parenteral formulations of morphine are used when oral administration of this agent is presumed ineffectual, classically in post-operative situations. Effective though routine intermittent injections are, they have their disadvantages: blood levels of morphine assume a compound sine-wave shape and, depending upon the frequency and dose of the injections, some patients are alternately obtunded and pain free, or very much alert and in considerable pain. Constant iv infusions with bolus doses on demand resolve the above problem and create others: iv lines occasionally clot and, if sometime later the clot is freed, a patient commencing to feel increasing pain inadvertently receives an excessive dose as a form of bolus injection; in addition, most constant infusions are administered by some form of mechanical pump and more than one patient has died because of "runaway" failure of the pump.

Finally, there are site-selective injections of morphine. Epidural and intrathecal infusions can provide profound regional analgesia with relatively small doses. However, these techniques require supervision by specialists well versed in the art of infusions in and around the spinal cord.

From the foregoing, it is apparent that a new mode of administration of morphine is desireable which permits both to bypass the vagaries of intestinal absorption and the first pass effect through the liver, and also to avoid the mechanical and infective problems associated with invasive parenteral technologies.

Passive transdermal administration of fentanyl has been described by Gale et al (U.S. Pat. No 4,588,580) and Cleary (U.S. Pat. No 4,911,916), while Aungst et al (EPA No 85109909.3) claimed a similiar technique for the administration of some 13 opioids and opioid antagonists. Passive transdermal administration of a drug, for example by patch application, relies ultimately on the concentration gradient to determine the rate of drug delivery and herein lie the advantages of this form of drug administration: it is the essence of simplicity with no delivery device to malfunction; in theory at least, blood levels of drugs reach a plateau and then maintain constant levels for many hours, or even days, on end; non-compliance by patients diminishes from a major to a minor issue.

In spite of these undeniable advantages, passive transdermal administration of opioids has some pertinent disadvantages: there is a time interval of at least 6 hours between the application of a fentanyl patch and the appearance of therapeutic blood levels, obviously rendering this technique useless for an acute situation; furthermore, this interval varies so widely that the patches are rarely used in post-operative situations where patients receive their opioids by the more controllable iv or im injections; finally, although the rate of fentanyl absorption is fairly constant for any one individual, the rates of absorption between two similiarly sized individuals may vary by as much as 100%, which adds to the uncertainty when these patches are applied for the first time.

Electromotive administration of drugs eliminates the most prominent disadvantages of passive transdermal drug delivery. For the purposes of this invention, Electromotive Drug Administration (EMDA) is defined as the combined or additive effects of iontophoresis and electrophoresis upon drug transport. As is known, iontophoresis is the active transport of ionised molecules into tissue by the passage of an electric current through a solution containing the ions, using an appropriate electrode polarity. Usually, the electrical driving force of administration is totally predominant over passive diffusion of the (drug) ions, leading to a greatly accelerated controllable rate of drug administration. In addition, iontophoresis is associated with increased transport of water into tissues (electroosmosis) which may induce an enhanced penetration of electrolytes (down their coulombic gradients) and non electrolytes or even the transport of electrolytes against their coulombic gradients, as described by Petelenz et al. (Journal of Controlled Release 1992; 20: 55–66). For the purposes of this invention and in accordance with Sibalis (U.S. Pat. No. 4,878,892), this phenomenon is termed electrophoresis and is a form of "solvent drag" where the gradient of the chemical potential for water activates both a flow of water and of solute dissolved in water. Usually the effect of iontophoresis predominates over electrophoresis with ionised drugs as, for example, drugs in the form of their water soluble salts.

Thus, it may be anticipated that EMDA of ionised drugs, for example of opioids such as of morphine, will result in accelerated administration rates with a consequent rapid rise of blood levels into the therapeutic range; the interval of time required to attain therapeutic blood levels is quite constant for individuals of similiar bodily mass when the same current strengths and times of application are used;

rates of opioid administration in different individuals depend solely upon the two controllable variables, current and time, not upon the totally uncontrollable vagaries of skin texture and thickness. The feasibility of iontophoretic administration of morphine has been demonstrated in clinical settings by Petelenz et al (U.S. Pat. Nos. 4,752,285 and 4,915,685); and by Ashburn et al, (J. Pain and Sympton Management 1992; 7(1):27–33) whose investigations showed clinically effective blood levels of morphine within 15–20 minutes of application of electric current. Petelenz et al (Transdermal drug delivery system for applications in space flight: Phase I Report. NASA SBIR Aug. 31, 1990) also conducted laboratory experiments with iontophoresis of fentanyl into and across hairless mouse skin.

All of the above investigations were successful in that therapeutic administration rates of the two opioids were achieved for periods of time extending into hours. Nevertheless, there were several well known iontophoretic problems to be solved before the desired results could be obtained. Charge transfer must take place at the solid conductor-electrolyte interface and, at the anode, there are only two mechanisms for charge transfer: dissolution of anodic metals adding metallic ions to the drug solution; or, with an anode of inert material, the build up of an electrical double layer at the interface causing the potential to rise until there is electrolysis of water, hydrogen ions ($H^+$) and gaseous oxygen ($O_2$). Both producing situations result in additional undesireable ions within the drug solution competing for electric charge and diminishing efficiency of drug delivery. Also, excessive quantities of $H^+$ rapidly acidify the electrode contents, possibly changing the chemical structure of the drug and eventually damaging the underlying skin. To avoid these problems, two different approaches were used. The first was the selection of the hydrochloride salt of morphine (MHCl) combined with the use of a silver anode, so that dissolution of silver into silver ions ($Ag^+$) resulted in the immediate precipitation of insoluble silver chloride (AgCl), thereby removing competitive $Ag^+$ and avoiding generation of $H^+$ (U.S. Pat. No. 4,752,185). The second approach was the attachment of the medication (morphine) to an ion exchange matrix so that when the drug ion left the matrix the vacated active sites were occupied by products of electrolysis which was purposely engendered at the anode-drug solution interface (U.S. Pat. No. 4,915,685).

Although these two techniques lead to satisfactory results in the laboratory and in a limited number of patients involved in clinical investigations, there are additional problems to be overcome. The silver-MHCl combination is very inefficient (9%–12%), i.e. shows a low current efficiency in drug transport, which is tolerable, and also leaves a great proportion of the morphine (80%–90%) remaining unused in the electrode-receptacle, which will create major problems in disposal if used on a wide scale. An ion exchange matrix, resin or membrane, theoretically will provide almost 100% utilization of morphine, however, preparation of both the drug itself and the drug containing electrode-receptacle increases the complexity of the apparatus.

SUMMARY OF THE INVENTION

It is a principal object of the invention to provide an improved formulation of the drug, morphine, in the form of derivatives thereof especially suitable for electromotive drug administration (EMDA).

It is a further object of the invention to provide an improved formulation of morphine suitable for EMDA administration which allows a higher drug utilization than possible with morphine hydrochloride, thus also minimizing the disposal problems relating to remaining amounts of non-used morphine existing with conventional morphine derivatives or formulations.

Still a further object is that of providing an improved morphine formulation which allows for an EMDA with improved efficiency of drug transport.

Yet a further object of the invention is that of providing an improved morphine formulation for use by EMDA without deleterious changes occurring in the pH of the drug medium during administration and accordingly without damaging the patient's skin.

These and other objects are achieved by an improved formulation of morphine according to the invention comprising one or more morphine citrate salts selected from those having the formula I:

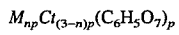

$$M_{np}Ct_{(3-n)p}(C_6H_5O_7)_p \qquad I$$

wherein M is protonated morphine, Ct is a physiologically acceptable cation, n is any integer or fractional number greater than zero and less than or equal to three ($0<n \leq 3$), and p is an integer from 1 to 3.

DETAILED DESCRIPTION OF THE INVENTION

Citric acid has three carboxyl groups, all or part of which can be salified by the morphine base. Thus the formulation of the present invention can comprise trimorphine citrate or mixed citrates of morphine and of a further cation, which is physiologically acceptable, or their mixtures. It is preferred that such further cation be monovalent, since citrate is a weak chelating agent and chelates formed with polyvalent cations could complicate the intended electromotive administration. Preferably, the further cation is selected from sodium and potassium cations.

The morphine citrate according to the invention can be prepared in the form of an aqueous solution, by adding morphine (formula II) for example morphine hydrate in a powder form to a solution of citric acid in such molar quantities that the morphine base is converted to protonated morphine (position 17) such that said conversion results in a solution approximating the formulation: $3M^+ (C_6H_5O_7)^{3-}$.

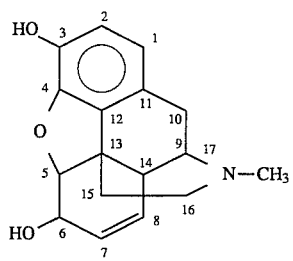

This particular process of the invention may be varied according to circumstances. For example, if the combination results in overt precipitation of morphine base (Mb), two additional procedures, not mutually exclusive, may be employed. They are:

1. Addition of small quantities of a strong acid, for example HCl, to lower the pH of the morphine solution to the point where the precipitated $M_b$ is largely converted to $M^+$.

2. Addition of ethanol to comprise 10%–30% (v/v) of the morphine citrate solution to act as a solubilizing reservoir for the non ionised morphine precipitating at higher pH values.

If it is desired to vary the buffering capacity of the morphine citrate, then citrate salts with said monovalent cations are added. This permits variation of the buffering capacity within wide limits. For example, the addition of trisodium (or tripotassium) citrate to a solution of trimorphine (10 mg/ml) citrate admixed with ethanol 20%–30% (v/v) is feasible until the pH reaches 8.0–8.1 units, at which point saturation of ethanol and precipitation of $M_b$ will occur. Up to this pH limit, the amount of citrate salt to be added may be varied: the larger the amount added, the greater the buffering capacity.

In another embodiment of the present invention, a pure aqueous solution of trimorphine citrate may be additionally buffered by judicious addition of the following combinations, using sodium citrate salts as an example:

$Na_3$ citrate+citric acid $Na_3$ citrate+$NaH_2$ citrate $Na_3$ citrate+$Na_2H$ citrate The precise proportions in each of these mixtures is so adjusted as to result in a pH 6–6.5 units in aqueous solution.

The addition of such citrate salts gives rise to mixed salts of citrates of morphine and sodium (or potassium) with variable proportions of the cations, as encompassed by the general formula I of morphine citrate salts according to the present invention. Although it was foreseeable that charge competition from introduced cations ($Na^+$, $K^+$) could have lowered the current efficiency of the drug delivery process, it was surprisingly found that such added citrate salts increased the administration rate of the drug.

The morphine citrate solutions prepared as above can have widely variable concentrations, such as from 1 to 80 mg/ml, in particular from 1 to 40 mg/ml. For most purposes a concentration of about 10 mg/ml will be suitable, for example for 12–24 hour post operative analgesia for most patients of all sizes and both sexes. An important point with ionised solutions placed in contact with the skin for the purpose of electromotive delivery, is that they should be preferably hypotonic with respect to the osmolarity of body tissue fluids: hypotonic solutions hydrate the resistive stratum corneum, providing more even distribution of electrical current and lower electrical resistance; hypertonic solutions dessicate the underlying skin, increasing the number of regions of current density and subsequent thermal damage. An isotonic solution of morphine citrate would contain approximate amounts of morphine, 30–80 mg/ml, depending upon the quantity of citrate buffer added.

It must be realised that certain persons (usually with cancer) with severe, prolonged pain and physiologically habituated to opioids, may require hundreds of milligrams of morphine daily. In these special circumstances, the use of morphine concentrations of 30–40 mg/ml may be advantageous. Conversely, infants and small children in post operative situations would require morphine at concentrations of 1–2 mg/ml.

For the purposes of electromotive administration, and in particular of iontophoretic administration, the morphine citrate, in addition to its aqueous solution form, can also be formulated in any form in which the morphine ions are free to move. In such formulations the medicament can be incorporated into a gel (such as gelatin), a hydrogel, a gum, a foam, or a nonionic cream so as to make the iontophoresis process convenient. Moreover, in the case of narcotics, the incorporation of the medicament into a cream or gel minimizes the possibility of the drug being improperly extracted from electrodes and misused.

These further formulations have the added advantage of not leaking so as not to create additional disturbance to the patient.

As said hereinbefore, the morphine citrate according to the invention is particularly suitable for electromotive administration.

The electromotive drug administration (EMDA) technique in this invention relies mainly on iontophoresis, i.e. active transport of ionized drug molecules into the tissue by the passage of electric current with electrophoresis contributing to a lesser, but still important, degree.

The morphine citrate formulation of the invention is administered by a normal iontophoretic device. For example the drug formulation is placed in a treatment (active) electrode-receptacle wherein the electrode is anodic and is made of substantially inert material.

For example inert anodes usable according to the invention are anodes made of carbon, gold, platinum and stainless steel.

Usually the electrically conductive anode is attached to a receptacle so as to form an electrode-receptacle which has to contain the drug solution in contact with the anode and with the patient's skin and avoid leakage of the solution to surrounding areas.

The receptacle is usually made of a non-conductive material, for example a polymer, and has a container configuration open at the bottom so as to be positioned on a skin area and to be sealed thereon, for example by adhesive means (tape, ribbon, plaster, etc.) so as to hold a liquid in contact with the respective skin area.

The anode proper can be attached by any appropriate known means to the internal wall of the receptacle so as to come into contact with the drug solution when this latter is introduced into the electrode-receptacle. For example the anode can be partly embedded in the receptacle side walls, or can be applied as a metal coating on part of the inner surface of the wall, or can be a conductive wire or plaque fixed by any appropriate means to the side wall of the receptacle.

Said electrode-receptacle is placed against the skin of the person to be treated and a dispersive, cathodic electrode is also placed on a skin area spaced apart from said treatment electrode. A voltage differential is then applied to the treatment (positive charge) electrode-receptacle and the dispersive (negative charge) electrode. The voltage and current are those commonly used in conventional iontophoretic drug delivery methods. As a result hydrogen ions are produced by hydrolysis of water in the drug solution contained in said treatment electrode. As it will be fully explained hereinbelow, at the concentrations of morphine citrate salts useful herein, the hydrogen ions are substantially buffered by citrate ions present in the formulation according to this invention, and electromotive forces administer morphine ions transdermally to the person to be treated without deleterious changes in pH occurring in the drug solution contained in the electrode-receptacle.

Moreover the citrate anion has three pKa levels, 3.13, 4.76 and 6.40 units, which permit a broad selection of pH ranges that can be applied safely to the skin. The three pKa values of the citrate anion permit the formation of a stable ionised salt with morphine whose pKa value is 8.2 units.

Furthermore, the morphine citrate formulation according to the invention theoretically attains a much higher efficiency and drug utilization than is possible with the morphine hydrochloride salt used in combination with a silver anode according to the known methods.

The Efficiency of drug transport is intended as the percentage of applied electric charge that is utilized in the transport of the drug ions. The efficiency depends, amongst other factors, upon the mobility of the ions present in the drug solution. In the case of morphine hydrochloride, MHCl, the high molecular weight of morphine (285 daltons) and its consequent low mobility, and the low molecular weight of chloride (35.5 daltons) and its consequent high mobility, give rise, as said before, to a low efficiency of about 9–12%.

In the case of the morphine citrate salts the molecular weight of the citrate (189 daltons) anion more closely matches that of morphine than does the chloride anion, whereby also its mobility is lower than that of chloride, approaching that of morphine. Consequently, an efficiency of drug delivery higher than 10% can be achieved with morphine in the citrate salt, theoretically up to 30%.

Actually efficiency is almost identical with Transference Number (tr) defined in U.S. Pat. No. 4,752,285, which represents the proportion of applied charge involved in the transport of drug ions, and for morphine (m) it takes the following expression:

$$trm = |z_m| \mu_m C_m / \Sigma |z_i| \mu_i C_i$$

where: z is the valency, $\mu$ the mobility, C the concentration and i the summation of all ions in solution.

Based on this equation, in a pure aqueous solution of trimorphine citrate, the products of the two ionic valencies and molar concentrations are equal (Equivalent), so that the ratio of the molecular weights of the two species provide a theoretical trm value of approximately 0.3, or an efficiency of approximately 30%, for the administration of morphine. As will be demonstrated in the examples given hereinbelow the measured efficencies of electromotive morphine administration from morphine citrate solutions were in good agreement with the theoretical prediction.

The Drug Utilization as defined in this invention, essentially refers to the proportion of drug that can be transported from the electrode-receptacle into the skin with continuously running electric current, and without deleterious changes in the rate of drug transport and pH values within the electrode-receptacle. Electromotive utilization of morphine from a solution of morphine hydrochloride with a silver anode, according to the prior art, is constrained to about 10% by the rapid conversion of chloride ion to insoluble silver chloride precipitate.

To estimate the administration rate of morphine iontophoresed from a solution of morphine HCl, an equation supplied by Phipps et al (U.S. Pat. Nos. 4,744,787 and 4,747,819), may be used to calculate the theoretical administration rate of morphine. The equation is:

$$R_m max = 3600 \, MI/F$$

where Rm max is the theoretical maximum amount (mg/hour) of morphine that can be administered, I is the current in milliamperes, M is the molecular weight of morphine and F is Faraday's constant.

Applying the Phipps equation:

Rm max=10.6 mg $mA^{-1}$ $h^{-1}$ with 100% efficiency of administration. With 12% efficiency (trm=0.12):

Rm=1.28 mg $mA^{-1}$ $h^{-1}$.

In unusually close agreement between theoretical prediction and measurement, Ashburn et al (J. Pain and Sympton Management 1992; 7(1), p 32) supply transport rates of morphine (in the hydrochloride formulation) across hairless mouse skin of 1.3 mg $mA^{-1}$ $h^{-1}$, when the efficiency is approximately 12%.

When administering MHCl with silver as the anode, the chloride ion is consumed (converted to AgCl) at about 10 times the rate that morphine ions are administered. Provided there is sufficient silver present, when the supply of Cl is exhausted, $Ag^+$ enter the drug solution, reducing still further the efficiency of morphine administration and staining the underlying skin jet black because of reaction with sulphur-containing amino acids: harmless in itself but not appreciated by the subjects. If the supply of silver runs out, the potential rises still further until there is hydrolysis of water, generation of $H^+$ and the consequent likelihood of chemical burns to the skin.

In effect, the utilization of morphine is only about 10% before all the chloride is consumed and deleterious electrochemical changes appear. Stated another way, if morphine 10 mg is administered over 4–6 hours (a standard dose) from an electrode-receptacle, the receptacle must contain about 100 mg of morphine, 90 mg of which must then be discarded. This implies the problem of the disposal of thousands, or even millions, of receptacles containing large quantities of morphine in order to satisfy regulatory requirements concerning opioids.

Thus, a solution to the problem of low morphine utilization is required and Phipps et al (U.S. Pat. Nos. 4,747,819 and 5,057,072) foreshadowed this when they claimed an inert electrode material with an intentionally selected drug in a weak base form and the weak base form of the drug is DOH. This is however not applicable to morphine. A common and useful concentration of morphine is 10 mg/ml or approximately $3.5 \times 10^{-2}$ molar. In these concentrations, the hydroxide form of morphine cannot exist in aqueous solution in any appreciable quantities. Hydroxide ions at $3.5 \times 10^{-2}$ molar concentrations represent a pH far in excess of the pKa of morphine which would precipitate out as the relatively insoluble, non ionised, base form.

The requirement for increased drug utilization is being solved by the morphine citrate formulation according to this invention.

Utilization of morphine in morphine citrate solution using an inert anode is constrained only by the decline in pH of the morphine citrate solution: a pH level of 3.5 units is the lower limit of tolerance for human skin. This allows for a much greater morphine utilization than possible according to the prior art.

In fact, in a solution of morphine citrate containing morphine 10 mg/ml, there are protonated morphine $3.5 \times 10^{-5}$ mols/ml or $3.5 \times 10^{-5}$ Equivalents/ml and citrate ions $3.5 \times 10^{-5}$ Eq/ml. According to Phipps et al (U.S. Patent No. 4,744,787), $H^+$ generation rate from an inert platinum electrode is approximately $3 \times 10^{-6}$ moles $mA^{-1}$ $h^{-1}$. With a constant 30% efficiency, administration of morphine 10 mg will require a total charge 3–4 mA.h, which will generate approximately $H^+$ $10^{-5}$ mols, superficially matching the total buffering capacity, $3.5 \times 10^{-5}$ mols, of citrate quite closely. However, total buffer saturation of citrate by hydronium ions requires that the pH levels in the morphine citrate solution fall to at least 3.13 units and probably lower, which would be damaging to skin. Therefore utilization of morphine will be substantially less than 100%, but greater than the 10% utilization from morphine hydrochloride. It was surprisingly found, as said before, that addition of buffers in the form of citrate salts to the drug solution, even though providing additional charge competition, not only improved the buffering capacity of morphine but also increased the drug utilization and the administration rate of morphine.

Thus the use of citrate ions in the morphine citrate formulation of the invention had as one of its results the buffering of the hydrogen ions produced at the inert anode and in the maintenance of the pH of the drug solution within acceptable limits for the duration of the drug delivery and thus in the prevention of pH changes deleterious to the patients.

The following examples serve to illustrate the invention but they are not intended to limit it thereto and must be so broadly interpreted.

Reference will be made in the examples to the drawings wherein.

EXAMPLE 1

Preparation of Trimorphine Citrate

Figure 1:
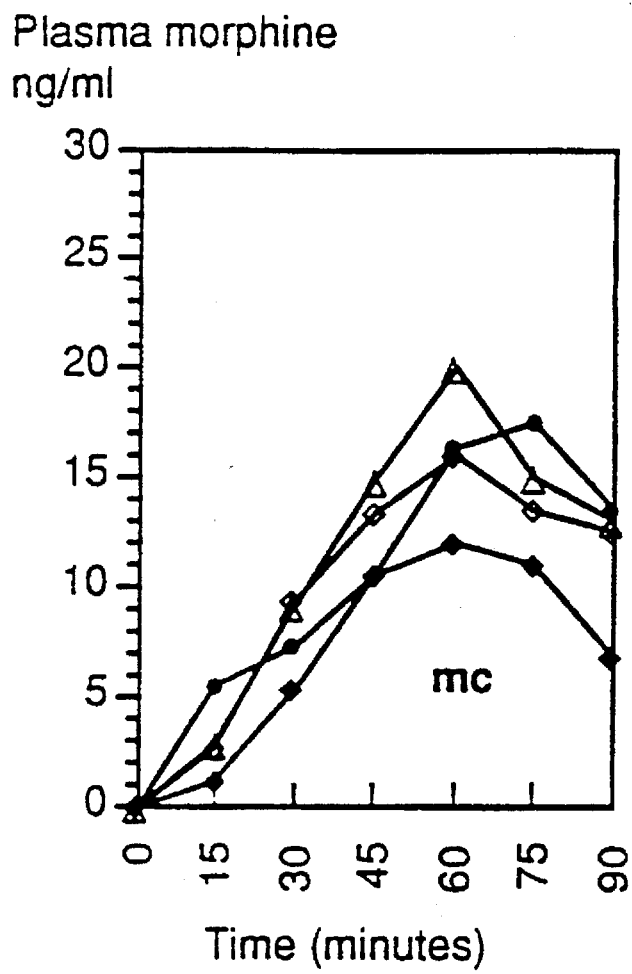
FIG. 1 is a graph showing the morphine plasma levels versus time during iontophoresis of morphine from trimorphine citrate (mc) according to this invention.
Figure 1:
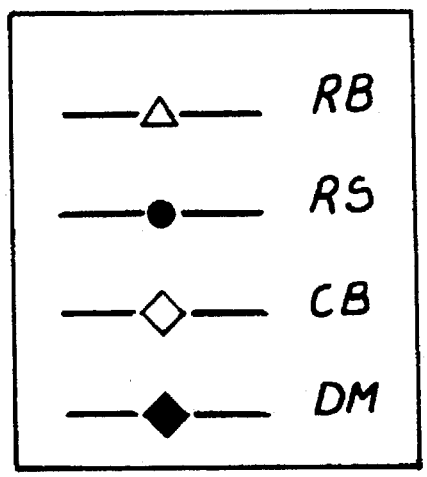

Citric acid powder, 2.1 grams, was dissolved in 1 liter of bidistilled water and the resulting pH of this dilute solution was approximately 3.0 units. To 100 ml of this citric acid solution hydrated morphine base powder ($M_b \cdot H_2O$) was added in 100 mg amounts, following each of which additions the mixture was stirred until morphine was completely dissolved and the pH was measured. Following addition of the 10th aliquot (1 gram total) there remained in suspension a small cloud of precipitate and the pH had risen to 6.5–7.0 units. After one hour at room temperature, with the small cloud of precipitate remaining settled at the bottom of the flask, it was resuspended evenly by stirring and shaking and 2.0 ml was withdrawn. To this small 2.0 ml aliquot was added 0.5 ml of 95% ethanol (20% v/v), the precipitate disappeared and pH remained at 6.5–7.0 units. To the 98 ml of pure aqueous solution remaining, HCl, N/2, was added in 0.2 ml aliquots with stirring to a total of 1.8 ml, at which point the precipitate disappeared and pH levels measured 6.0–6.3 units. Thus, there was formulated 100 ml of aqueous trimorphine citrate at a concentration of 9.4 mg/ml (morphine base powder was in the monohydrate form).

EXAMPLE 2

Preparation of Morphine Sodium Citrate

Following an initial series of iontophoretic experiments, it was decided to increase the buffering capacity of the morphine citrate solution. Trial and error experiments with $Na_3$ citrate and $Na_2H$ citrate mixtures demonstrated that equimolar parts of each resulted in dilute solutions ($\leq 0.3\%$) with a pH of 6.0–6.3 units. To 67 ml of the trimorphine citrate solution prepared as in Example 1, was added $Na_2H$ citrate, 97 mg, and $Na_3$ citrate, 107 mg, which dissolved without difficulty, no precipitate appeared and the pH remained at approx 6.0 units. The combined quantities of added citrate were calculated as equimolar to that in the 67 ml of trimorphine citrate solution so that the resulting solution had the empiric formula,

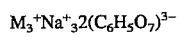

wherein M is morphine.

EXAMPLE 3

Iontophoresis of Morphine Citrate

Four volunteers, (RB, RS, DM, CB) underwent preliminary studies with iontophoresis of trimorphine citrate (mc). Conditions were standardised: an iv cannula for blood draws was inserted into the left forearm, the anodic active electrode (carbon)-receptacle containing 4 ml of mc (morphine concentration 9.4 mg/ml) was placed on the anterior aspect of the right forearm near to the elbow and the dispersive electrode on the right forearm near to the wrist. No electric current was used for the initial 30 minutes. Then, at time zero (0), current was applied, advancing to 2 mA in two minutes and was then stabilised at this level for a further 58 minutes: one hour total time with current running. Blood samples for morphine plasma levels were withdrawn at times −30, −15, 0 (no current); 5, 10, 15, 20, 30, 45, 60 minutes (current); and at 75 and 90 minutes (no current). Measurements of pH in the electrode-receptacle were performed at −30, −15, 0, 15, 30, 45 and 60 minutes. Finally, in an effort to obtain some mass balance results, morphine levels in the electrode were measured pre and post treatments.

Clinically, to varying degrees, all subjects displayed the signs and symptoms of opioid administration: dry mouth, congested nasal passages, constriction of pupils and lethargy. Also, within 10 minutes of the onset of electric current, all subjects demonstrated a red flare in the skin (histamine release) advancing outwards from the periphery of the electrodes.

Plasma morphine levels were measured in duplicate using a Radio Immune Assay (RIA) technique which is highly specific for free (unconjugated) morphine and has an accuracy of $\pm 1$ µg/ml. The results are displayed graphically in FIG. 1 and, as can be seen, plasma morphine levels were effectively zero prior to beginning electric current, climbed to therapeutic levels ($\geq 8$ µg/ml) within 45 minutes in all subjects and then declined when the current was switched off at 60 minutes. There is also an approximate inverse correlation between plasma levels and the size of the body pool: the respective weights of the subjects were DM 92 kg, RS 82 kg, CB 78 kg, RB 45 kg.

Efficiency of morphine administration is calculated from mass balance of morphine in the electrodes pre and post treatments. Use of the RIA technique presented some difficulties because electrode samples required dilutions of 100,000 fold. Nevertheless, the average quantity of morphine administered to the subjects was measured as 5.0 mg over one hour using a current of 2 mA; i.e. Rm=2.5 mg $mA^{-1}$ $h^{-1}$. This represents a trm value of 0.24 or 24% efficiency, which is in reasonable agreement with the theoretical values of efficiency set forth above as achievable with the present invention.

Figure 2:
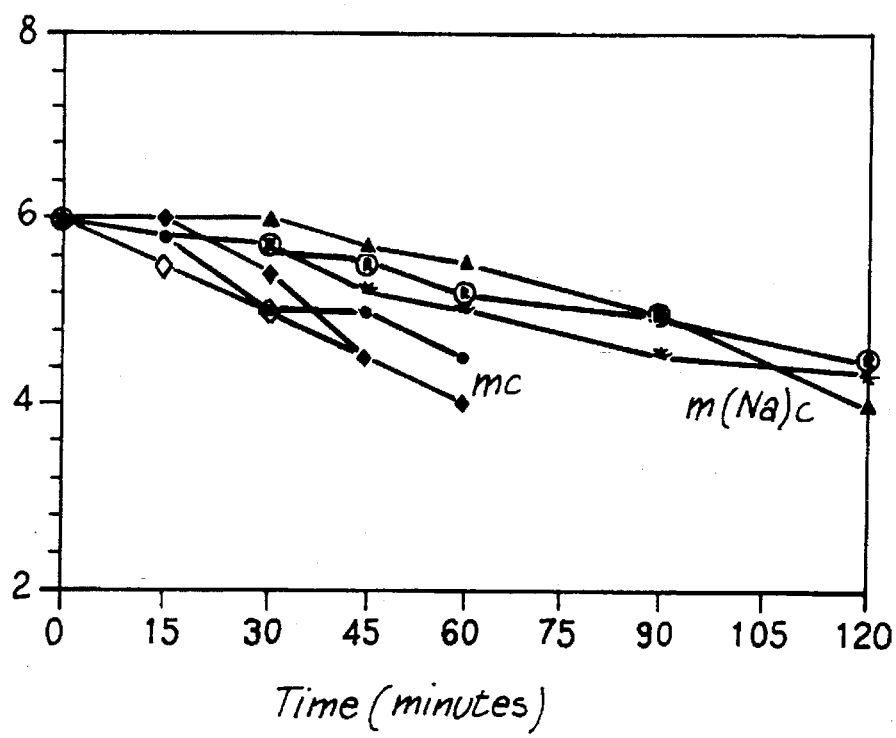
FIG. 2 is a graph showing the pH levels at the active electrode versus time during EMDA of trimorphine citrate (mc) and morphine sodium citrate m(Na)c according to the invention.
Figure 2:
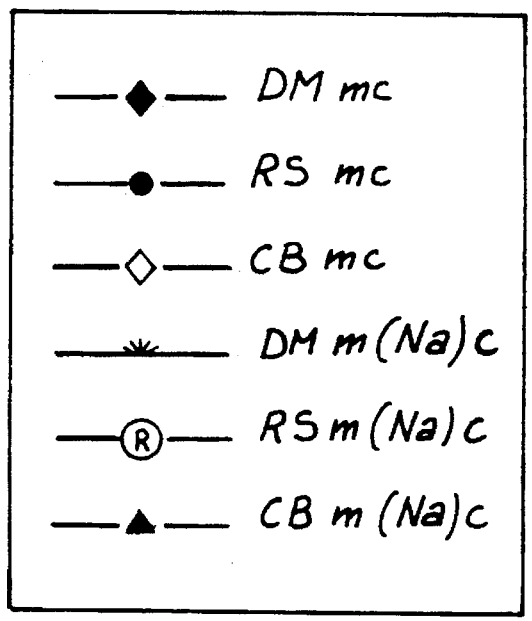

The percentage of morphine (in the electrode-receptacles) administered over one hour is calculated from the mass balance results: each electrode contained morphine 4×9.4≈38 mg total, therefore administration of an average morphine 5 mg defines the percentage administered as 13%. However, this figure does not represent the utilization as the pH values at the end of one hour were 4.0–4.6 units (FIG. 2) which are above the stated lower limit of 3.5 units. Extrapolation of pH values to 3.5 units indicates a 90 minute cut off in treatment times. Under the same experimental conditions, morphine 7.5 mg will be administered over 90 minutes, which represents a utilization of 20%.

EXAMPLE 4

Electromotive Administration of
$M_3^+Na_3^+2(C_6H_5O_7)^{3-}$

Electromotive administration of $M_3Na_3(C_6H_5O_7)_2$ in 3 of the 4 previous volunteers, RS, DM, CB, was conducted 5 days after the investigations described above. Experimental conditions were identical except: 1) The current of 2 mA was applied for 2 hours: and 2) blood samples were drawn for 60 minutes post treatment.

Figure 3:
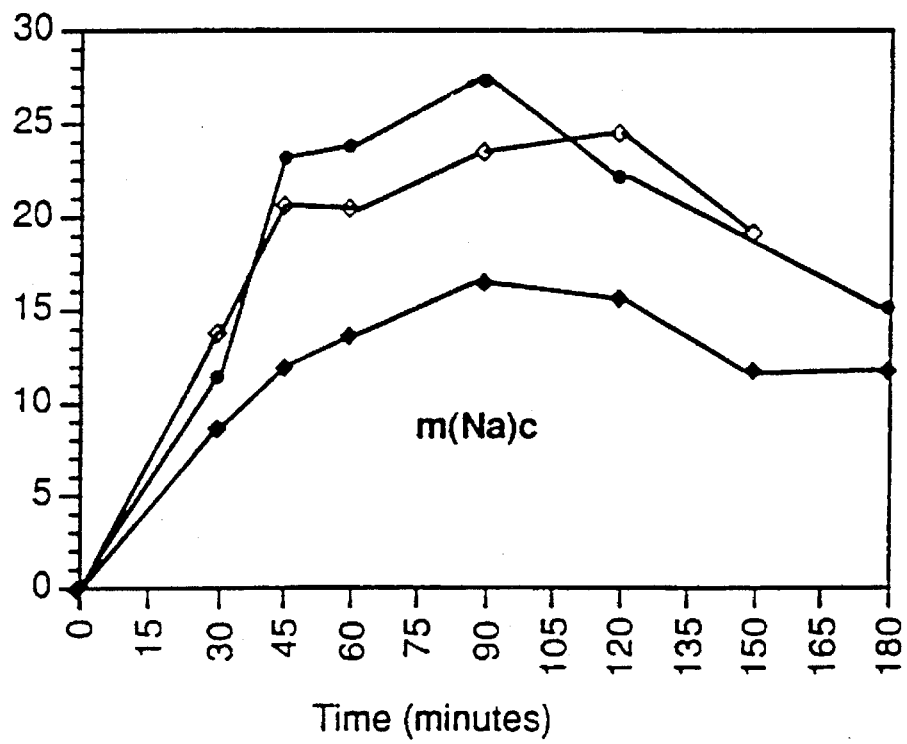
FIG. 3 is a graph showing the morphine plasma levels versus time during EMDA of morphine sodium citrate according to the invention.
Figure 3:
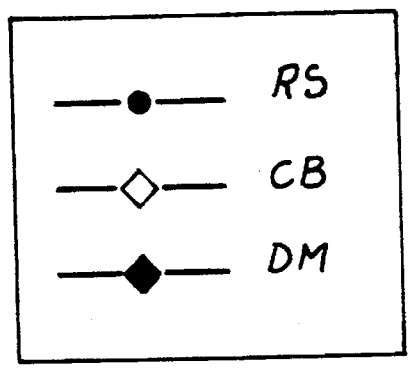

Clinically, the symptomatology resembled that in the first series of studies but was more marked. Plasma levels of morphine are shown in FIG. 3 and, as can be seen, morphine blood levels were essentially zero for the first 30 minutes (no current), then reached therapeutic levels within 30 minutes or less following application of electric current and finally plateaued at about 90 minutes. As anticipated, pH levels declined more slowly (FIG. 2: mNaC) than in the experiments with trimorphine citrate (FIG. 2: mc) and fell from about 6.0 to about 4.5 units over 2 hours of application of electric current at 2 mA.

It was surprising that the addition of equimolar quantities of sodium citrate to the trimorphine citrate solution enhanced the rate of morphine administration. Over the initial 90 minutes (−30 min. to +60 min.) of both series of experiments, conditions were virtually identical: the three subjects were the same individuals in both experimental series, placement of electrodes was confined to the right forearm, electric currents were identical and plasma measurements were undertaken in the same laboratory using the same R.I.A. technique. It would have been expected that addition of sodium citrate, particularly of the mobile sodium ion, would have provided increased charge competition and thereby would have reduced the rate of morphine administration. Nevertheless, at coincident times of blood draws, plasma levels of morphine were significantly elevated in the second series of experiments (morphine sodium citrate) in all three subjects (Table I). For example, at 60 minutes the comparable levels (μg/ml) were: DM: 11.4 and 13.6; RS: 16.5 and 23.7; CB: 16.0 and 20.4.

TABLE I

Plasma morphine levels and electrode pH values during
EMDA of mc and m(Na)c at times of coincident blood draws.

| Subject | Time of Blood Draw Minutes | Morphine Plasma Levels (mg/ml) mc | m(Na)c | Electrode pH mc | m(Na)c |
|---|---|---|---|---|---|
| DM | 30 | 5.4 | 8.6 | 5.4 | 5.7 |
|  | 45 | 10.1 | 11.9 | 4.6 | 5.5 |
|  | 60 | 11.4 | 13.6 | 4.1 | 5.0 |
| RS | 30 | 7.3 | 11.4 | 5.0 | 5.7 |
|  | 45 | 10.5 | 23.1 | 5.0 | 5.7 |
|  | 60 | 16.5 | 23.7 | 4.6 | 5.2 |
| CB | 30 | 9.3 | 13.6 | 5.0 | 6.0 |
|  | 45 | 13.4 | 20.6 | 4.6 | 5.8 |
|  | 60 | 16.0 | 20.4 | 4.0 | 5.6 |

Mass balance studies yielded an average amount of morphine 11.6 mg administered over two hours with a current of 2 mA. Strict adherence to the definitions of "trm" (Transferance Number for Morphine, according to U.S. Pat. No. 4,752,285) and "Efficiency" as provided in this application make it impossible to calculate their values. However, the combined effects of iontophoresis and electrophoresis result in a value which is equivalent to 27% efficiency of morphine administration. The percentage of morphine in the electrodes administered over two hours was 31% with the final pH measured at approximately 4.5 units. Again, by extrapolation (FIG. 2) to a pH of 3.5 units, the cut off is at 180 minutes, indicating a total amount of morphine 17 mg that may be administered. Thus, the utilization of morphine rises to 46%.

Conventional wisdom holds that introduction of buffers, in the form of small ionic species, to a drug solution lowers the rate of drug administration because of increased charge competition (U.S. Pat. No. 4,752,285). Occasionally, this approach is selected as the lesser of two evils in order to increase ionic strengths, and hence conductivity, in low molar concentrations of a drug solution and/or to neutralise the products of hydrolysis of water: generation of excess hydronium ions is especially pernicious because of their high mobility and their propensity to damage living tissues. In effect, there is exchanged a lower initial rate of drug delivery for a more consistent, prolonged delivery rate consequent upon a more stable pH in the drug solution.

This same conventional wisdom does not hold true for admixture of sodium citrate with morphine citrate as described in this invention. Inspection of Table 1 reveals that, during application of electric current at times of coincident blood draws in the three subjects involved in both series of experiments:

(a) All 9 morphine plasma levels resulting from administration of m(Na)c are higher than the corresponding levels resulting from administration of mc.

(b) All pH levels measured in m(Na)c electrodes are higher than those measured in mc electrodes.

(c) pH levels in the mc electrodes range 4.0–5.4 units.

The morphine concentration, 9.4 mg/ml ($3.2 \times 10^{-2}$ molar), used in all experiments does not represent a particularly low ionic concentration and charge competition offered by $H^+$, $10^{-4}$–$6 \times 10^{-6}$ molar is marginal to negligible even allowing for the great mobility of $H^+$.

Thus, it is postulated that electrophoresis as defined in this invention and which is governed by the coupling of the gradient of a particular species in solution to that of water, is more important than originally anticipated. In common with certain other solutes described by Sibalis (U.S. Pat. No. 4,878,892), sodium citrate enhances the negative gradient of chemical potential for water to such a degree that increased electrophoretic transport of morphine more than compensates for the expected decreased efficiency of iontophoretic administration. Under these circumstances, the term "iontophoresis" is incomplete and only partially accurate when applied to administration of morphine from m(Na)c solutions. Therefore, the inventors have applied the term electromotive drug administration to compensate for this deficiency where appropriate.

What is claimed is:

1. An improved morphine formulation specifically designated for electromotive administration, comprising at least a morphine-cation-citrate salt selected from the group of the formula:

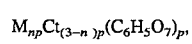

wherein
M is protonated morphine, Ct is a physiologically acceptable cation, n is any integer or fractional number greater than zero and less than three (0<n<3), and p is an integer from 1 to 3.

2. A formulation according to claim 1, in the form of an aqueous solution.

3. A formulation according to claims 1 or 2, wherein said morphine-cation-citrate salt has a concentration of 1 to 40 mg/ml.

4. A formulation according to claim 1, wherein said cation is selected from the group consisting of sodium and potassium ions.

5. Electromotive administration of a therapeutic dose of an improved morphine formulation comprising at least a morphine-cation-citrate salt selected from the group of the formula:

$$M_{np}Ct_{(3-n)p}(C_6H_5O_7)_p,$$

wherein M is protonated morphine, Ct is a physiologically acceptable cation, n is any integer or fractional number greater than zero and less than three (0<n<3), and p is an integer from 1 to 3, said administration being performed by applying an electric current through a substantially inert anode attached to a receptacle containing said formulation and placed against the skin of the patient in need of the treatment.

6. Electromotive administration according to claim 5, wherein said anode is selected from the group consisting of conductive carbon, gold, platinum and stainless steel.

* * * * *

UNITED STATES PATENT AND TRADEMARK OFFICE
CERTIFICATE OF CORRECTION

PATENT NO. : 5,607,940
DATED : March 4, 1997
INVENTOR(S) : Stephen, Robert et al It is certified that error appears in the above-indentified patent and that said Letters Patent is hereby corrected as shown below:

On the title page: Item [73] Assignee should read -- Physion S.r.l. Via Mantovani, 9 , 41037 Mirandola (Prov. of Modena), Italy --.

Signed and Sealed this

Twenty-sixth Day of August, 1997

Attest:

BRUCE LEHMAN

Attesting Officer

Commissioner of Patents and Trademarks